US00PP19791P3

(12) United States Plant Patent
Blom

(10) Patent No.: US PP19,791 P3
(45) Date of Patent: Mar. 3, 2009

(54) ***CHRYSANTHEMUM* NAMED 'ZANMUFIVE'**

(50) Latin Name: *Chrysanthemum morifolium L.*
Varietal Denomination: Zanmufive

(75) Inventor: Wilhelmus Bernardus Blom, GA Leimuiden (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 0 days.

(21) Appl. No.: 11/783,591

(22) Filed: Apr. 10, 2007

(65) Prior Publication Data

US 2008/0295209 P1 Nov. 27, 2008

(51) Int. Cl.
*A01H 5/00* (2006.01)

(52) U.S. Cl. ..... Plt./293; Plt./287

(58) Field of Classification Search ..... Plt./287, Plt./293

See application file for complete search history.

*Primary Examiner*—Annette H Para
*Assistant Examiner*—Louanne C Krawczewicz
(74) *Attorney, Agent, or Firm*—Steptoe & Johnson LLP

(57) ABSTRACT

A *chrysanthemum* plant named 'Zanmufive' characterized by its medium sized blooms with red ray florets and prolific branching; natural season flower date September 4–8; blooming for a period of 5 weeks.

3 Drawing Sheets

Botanical designation: *Chrysanthemum morifolium* L.
Cultivar denomination: 'ZANMUFIVE'.

BACKGROUND OF THE INVENTION

'Zanmufive' is a product of a breeding and selection program for outdoor pot mums (garden mums) which had the objective of creating new *chrysanthemum* cultivars with a decorative type flower, a natural season flower date around September 4–8; blooming for a period of 5 weeks. The new plant of the present invention comprises a new and distinct cultivar of *chrysanthemum* plant 'Zanmufive' is a seedling resulting from a crossing program, set up by a previous breeder, and which records are unknown to the inventor. The new and distinct cultivar was discovered and selected as a flowering plant by Wilhelmus Bernardus Blom on a cultivated field in Rijsenhout, The Netherlands in 2005. The first act of asexual production of 'Zanmufive' was accomplished when vegetative cuttings were taken from the initial selection in 2005 and propagated further in a controlled environment in Rijsenhout, The Netherlands. The new cultivar has been found to retain its distinctive characteristics through successive propagations.

BRIEF DESCRIPTION OF THE PHOTOGRAPHS

The present invention of a new and distinct variety of *chrysanthemum* is shown in the accompanying drawings, the color being as nearly true as possible with color photographs of this type. Pictures were taken of 16 week old plants.

DESCRIPTION OF THE INVENTION

Figure 1:
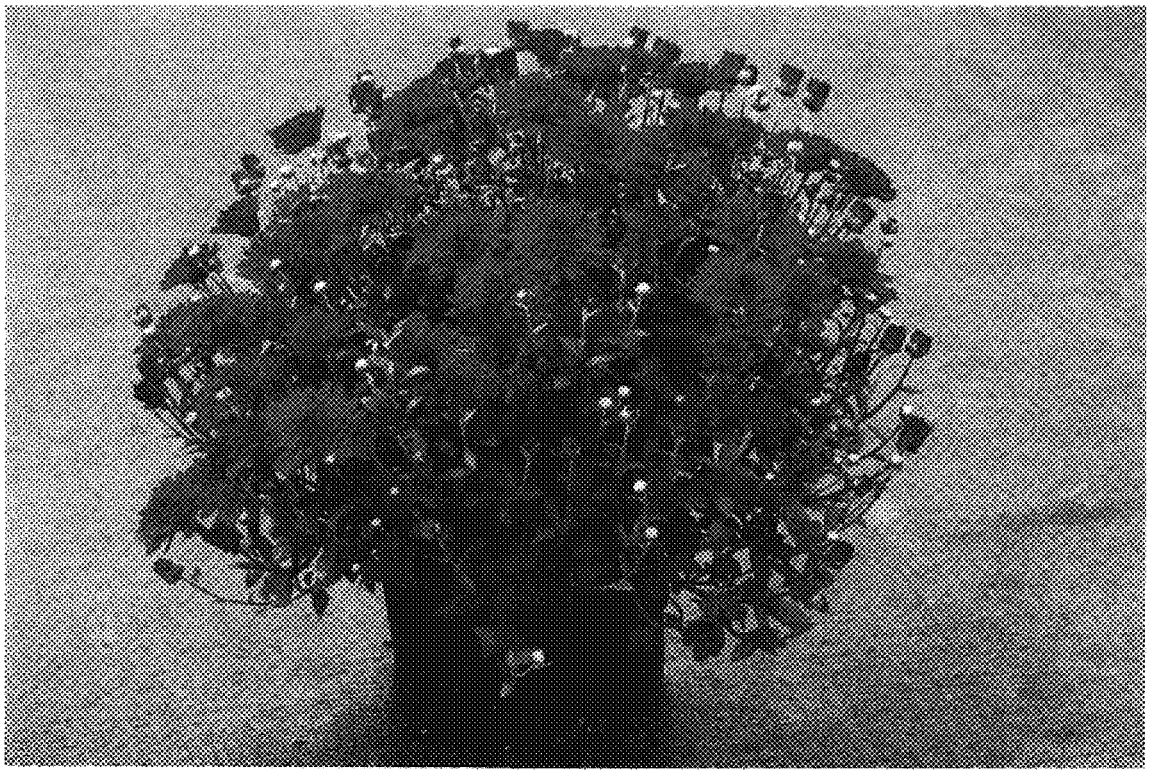
FIG. 1 shows a plant of the cultivar in fill bloom
Figure 2:
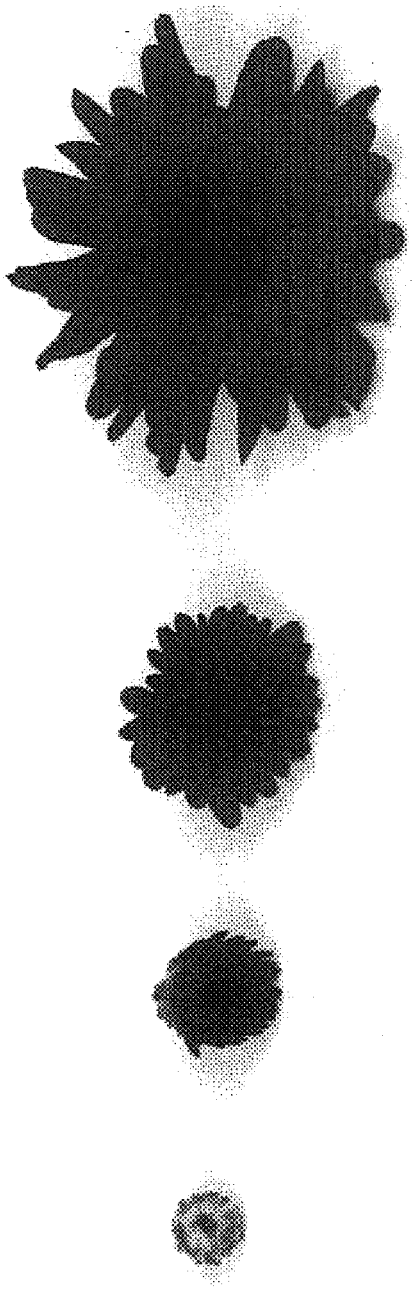
FIG. 2 shows the various stages of bloom of the new cultivar.
Figure 3:
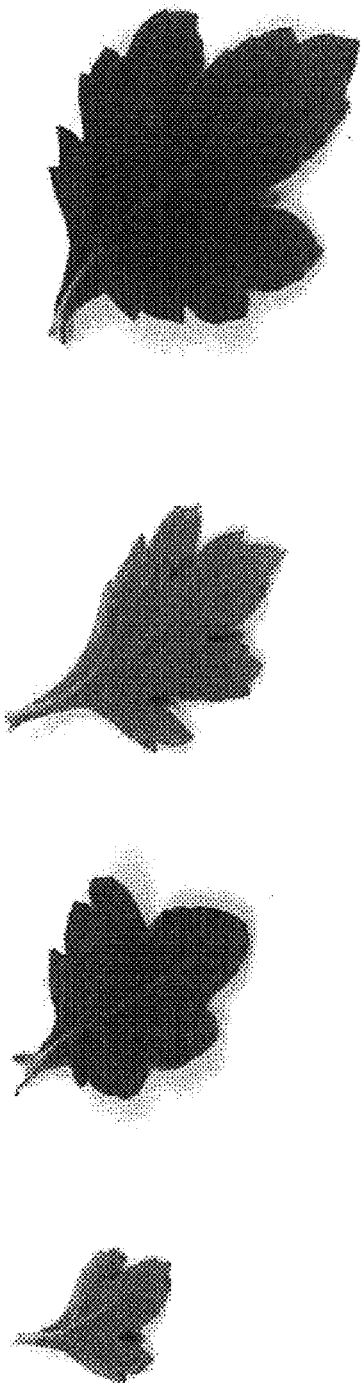
FIG. 3 shows the various stages of foliage of the new cultivar.

This new variety of *chrysanthemum* is of the botanical classification *Chrysanthemum morifolium* L. The observations and measurements were gathered from plants grown out door in Rijsenhout, The Netherlands under natural day length and temperature and planted in week 24 in 2006. The natural blooming date of this crop was September 4–8 (week 36). The average height of the plants was 28 cm. No growth retardants were used. No tests were done on disease or insect resistance or susceptibility. No tests were done on cold or drought tolerance. This new variety produces medium sized blooms with red ray florets blooming for a period of 5 weeks.

From the cultivars known to inventor the most similar existing cultivar in comparison to 'Zanmufive' are 'Plutores' (U.S. Plant Pat. No. 12,919) and 'Manakin' (U.S. Plant Pat. No. 11,521) When 'Plutores', 'Manakin' and 'Zanmufive' are being compared the following differences are noticed: The differences of 'Plutores', 'Manakin' and 'Zanmufive' are (1) Flower type, (2) Flower size and (3) Natural season flowering time (1) The flower type of 'Manakin' is single, while that of 'Plutores' and 'Zanmufive' is double (2) The flowers of 'Manakin' and 'Zanmufive' are smaller than those of 'Plutores' (3) The plants of 'Plutores', 'Zanmufive' and 'Manakin' flower at different times, resp. in late August, early and mid-September.

The following is a description of the plant and characteristics that distinguish 'Zanmufive' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *chrysanthemum* plant 'Zanmufive'

| | |
|---|---|
| Bud | |
| Size | Small; cross-section 0.5 cm, height 0.4 cm |

TABLE 1-continued

| Botanical Description of *chrysanthemum* plant 'Zanmufive' | |
|---|---|
| Shape | Spherical |
| Texture | Pubescent |
| Outside Colour | Greyed green 192A |
| Phyllaries | |
| Number | 15, arranged in 3 rows |
| Shape | Elliptic |
| Apex | Acute |
| Base | Truncate |
| Margin | Entire |
| Colour | Green 138A |
| Length and width | 7 mm and 3 mm |
| Texture | Pubescent |
| Presence among disc-florets | Not present |
| Bloom | |
| Type | Double |
| Height | 1-1.3 cm |
| Size | 4.5 cm |
| Peduncle length | 7 cm |
| Peduncle color | Greyed purple N 186C |
| Peduncle diameter | 1 mm |
| Peduncle surface | Ribbed |
| Number of blooms per branch | Approx. 5 blooms |
| Performance on the plant | 5 weeks |
| Seeds | Produced in small quantities, ovate grey-brown 199A, 1½ mm in length. |
| Fragrance | Faint *chrysanthemum* odor |
| Color | |
| Center of the flower | Immature stage: Red-purple 59A<br>Mature stage: Red-purple 59A |
| Color of upper surface of the ray-florets | Red 46A |
| Color of the lower surface of the ray-florets | Greyed red 181A |
| Tonality from Distance | A garden mum with red flowers |
| Color of the ray-florets after aging of the plant | Greyed purple 185B |
| Ray florets | |
| Texture | Upper surface: Satiny<br>Lower surface: Smooth |
| Number | 130-140 |
| Shape | Oblong |
| Apex | Rounded |
| Base | Attenuate |
| Cross-section | Flat |
| Longitudinal axis of majority | Straight |
| Length of corolla tube | 0.3-0.4 cm |
| Ray-floret margin | Entire |
| Ray-floret length | 1.8-2 cm |
| Ray-floret width | 0.4-0.5 cm |
| Ratio length/width | Medium |
| Shape of tip | Rounded |
| Disc florets | Absent |
| Receptacle | |
| Shape | Conical raised |
| Height | 2.5 mm |
| Diameter | 2 mm |
| Reproductive Organs | |
| Androecium | Absent in ray florets |
| Pollen | None |
| Gynoecium | Present in ray florets |
| Styles | Thin |

TABLE 1-continued

| Botanical Description of *chrysanthemum* plant 'Zanmufive' | |
|---|---|
| Style color | Yellow 13A |
| Style Length | 0.3 cm |
| Stigma color | Yellow-green 144A |
| Stigma Width | 1 mm |
| Ovary | Enclosed in calyx |
| Plant | |
| Form | Grown as a spray type potmum, outdoor mounded and round |
| Growth habit | Spherical shape |
| Growth rate | Medium to high |
| Height | 25-28 cm |
| Width | 44-45 cm |
| Stem Color | Greyed-brown 199C |
| Stem Strength | Strong |
| Stem Brittleness | Not brittle |
| Stem Anthocyanin Coloration | Greyed purple N186C |
| Internode length | 1-2 cm |
| Length of lateral branch | From top to bottom 20 cm |
| Lateral branch color | Greyed Green 195A with streaks of Greyed purple N 186C |
| Lateral branch, attachment | Strong |
| Branching (average number of lateral branches) | Prolific with 9-10 breaks after pinching |
| Natural season blooming date | September 4-8 |
| Foliage | |
| Leaf color | Upper side Green 138A<br>Lower side Green N138B |
| Color midvein | Upper side Yellow green 147D<br>Lower side Yellow green 148D |
| Size | Small.; length 3.5-4.5 cm, width 2.5-3.5 cm |
| Quantity (number per lateral branch) | 15-16 |
| Shape | Widely elliptic |
| Texture upper side | Glabrous |
| Texture lower side | Pubescent |
| Venation arrangement | Palmate |
| Shape of the margin | Serrated |
| Shape of Base of Sinus Between Lateral Lobes | Rounded |
| Margin of Sinus Between Lateral Lobes | Diverging |
| Shape of Base | Obtuse |
| Apex | Mucronulate |
| Petiole length | 0.5-1 cm |
| Petiole diameter | 1.5-2 mm |
| Petiole texture | Pubescent |
| Petiole color | Yellow-Green 147D |

TABLE 2

| Differences with the comparison varieties | | | |
|---|---|---|---|
| | 'Zanmufive' | 'Plutores' | 'Manakin' |
| Flower type | double | double | single |
| Flower size | 4.5 cm | 5-5.5 cm | 3.8 cm |
| Natural season flowering date | Early September | Late August | Mid September |

I claim:

1. A new and distinct variety of *chrysanthemum* plant as described and illustrated.

* * * * *